(12) United States Patent
Kenmochi et al.

(10) Patent No.: US 7,640,638 B2
(45) Date of Patent: Jan. 5, 2010

(54) FASTENING SYSTEM FOR WEARING ARTICLE

(75) Inventors: Yasuhiko Kenmochi, Kagawa-ken (JP);
Akiyoshi Kinoshita, Kagawa-ken (JP);
Natsuko Aoyagi, Kagawa-ken (JP);
Kayoko Tanaka, Kagawa-ken (JP);
Yusuke Kawakami, Kagawa-ken (JP)

(73) Assignee: Uni-Charm Corporation, Ehime (JP)

( * ) Notice: Subject to any disclaimer, the term of this patent is extended or adjusted under 35 U.S.C. 154(b) by 355 days.

(21) Appl. No.: 11/773,402

(22) Filed: Jul. 3, 2007

(65) Prior Publication Data

US 2008/0016656 A1    Jan. 24, 2008

(30) Foreign Application Priority Data

Jul. 6, 2006    (JP) .............................. 2006-187146

(51) Int. Cl.
*A44B 18/00* (2006.01)
(52) U.S. Cl. ....................................... 24/442
(58) Field of Classification Search ........................ None
See application file for complete search history.

(56) References Cited

U.S. PATENT DOCUMENTS

| | | | | |
|---|---|---|---|---|
| 4,884,323 A * | 12/1989 | Provost et al. | ................. | 24/442 |
| 5,108,384 A * | 4/1992 | Goulait | ...................... | 604/390 |
| 5,123,467 A * | 6/1992 | Steinberg | .................... | 150/106 |
| 5,176,670 A * | 1/1993 | Roessler et al. | ............. | 604/391 |
| 5,279,604 A * | 1/1994 | Robertson et al. | ........... | 604/389 |
| 5,549,591 A * | 8/1996 | Landvogt | .................... | 604/389 |
| 5,785,699 A * | 7/1998 | Schmitz | ....................... | 604/391 |
| 5,795,350 A * | 8/1998 | Schmitz | ....................... | 604/391 |
| 5,897,545 A * | 4/1999 | Kline et al. | ................. | 604/386 |
| 5,996,189 A * | 12/1999 | Wang | .......................... | 24/451 |
| 6,447,497 B1 | 9/2002 | Olson | | |
| 6,546,603 B1 * | 4/2003 | Wang et al. | ................... | 24/451 |
| 6,728,998 B2 * | 5/2004 | Wang et al. | ................... | 24/451 |
| 6,736,804 B1 * | 5/2004 | Robertson et al. | ...... | 604/385.13 |
| 7,425,242 B2 * | 9/2008 | Olsson et al. | ............... | 156/204 |

(Continued)

FOREIGN PATENT DOCUMENTS

WO    WO 03/082167    10/2003

*Primary Examiner*—Jack W. Lavinder
(74) *Attorney, Agent, or Firm*—Brinks Hofer Gilson & Lione

(57) ABSTRACT

A fastening system for a wearing article comprising a pair of hook carrying side edge portions with a hook component and a pair of loop carrying side edge portions with a loop component adapted to be detachably engaged with each other. Each of the hook carrying side edge portions comprises a first sheet section extending outward from each of the transversely opposite side edges of the wearing article, a second sheet section being contiguous to an outer side edge of the first sheet section so as to extend toward the transverse side edge, a joining area extending in parallel to and spaced from the outer side edge so as to join the first and second sheet section to each other, and a non-joining area surrounded by the joining area, the first and second sheet sections and the outer side edge, and the hook component has first and second edges extending in parallel to the outer side edge and is secured to the hook carrying side edge portion in such a manner that the first side edge lies in the joining area while the second side edge lies in the non-joining area.

5 Claims, 5 Drawing Sheets

U.S. PATENT DOCUMENTS

| | | | |
|---|---|---|---|
| 7,503,912 B2 * | 3/2009 | Otsubo et al. | 604/387 |
| 7,534,237 B2 * | 5/2009 | Olson et al. | 604/389 |
| 2003/0009144 A1 * | 1/2003 | Tanzer et al. | 604/391 |
| 2003/0014033 A1 * | 1/2003 | Back | 604/391 |
| 2005/0043698 A1 | 2/2005 | Otsubo et al. | |
| 2008/0097368 A1 * | 4/2008 | Molander | 604/391 |
| 2008/0125736 A1 * | 5/2008 | Kline et al. | 604/370 |

* cited by examiner

FASTENING SYSTEM FOR WEARING ARTICLE

BACKGROUND OF THE INVENTION

The present invention relates generally to a fastening system for a wearing article and particularly to such a fastening system for a disposable diaper.

There are well known fastening systems for connect front and rear waist regions of a wearing article by means of a mechanical fastener comprising a hook component and a loop component detachably engageable with the hook component. For example, National Publication of translated version No. 2002-532147 (hereinafter referred to as "Reference 1") discloses a diaper adapted to be fastened around a diaper wearer's body by means of the mechanical fasteners respectively provided on transversely opposite side edges of the diaper. The diaper disclosed therein adopts the fastening system having the hook component 107 provided on an outer side of the diaper as illustrated in FIG. 5A in the accompanying drawing of the present specification, taking account of a possibility that it might create a feeling of discomfort against the wearer if the hook component 107 come in contact with the wearer's skin.

However, even in the case of such a fastening system having the hook element 107 protruding outward with respect to the wearer's body, it is likely that the hook component 107 might be curled as illustrated in FIG. 5B and irritate the wearer' skin if a force F functioning to disengage the hook component 107 from the loop component is exerted on a free end 113 of a attachment sheet 120 carrying the hook component 107.

Japanese Unexamined Patent Application Publication No. 1997-191908 (hereinafter referred to as "Reference 2") discloses a fastening system having a construction as illustrated in FIG. 5C, wherein the hook component 107 is bonded to the attachment sheet 120 through the intermediary of a base sheet 105 which is, in turn, provided on its rear surface with a joining area 114 and a non-joining area 115 to the diaper, and the non-joining area 115 is located aside toward the free end 11 of the hook component 107. With this fastening system, it is unlikely that the hook component 107 might be easily disengaged from the loop component 108 even if the hook component 107 is moved so as to be vertically spaced from the loop component 108.

In the case of the fastening system disclosed in Reference 2, the base sheet 105 is provided on its rear side with the joining area 114 and the non-joining area 115 to the attachment sheet 120. Such an arrangement certainly ensure that a section of the attachment sheet 120 extending from a border 127 between the joining area 114 and the non-joining area 115 to the free end 113 is deformed, as illustrated in FIG. 5C, in response to the force F oriented to disengage the hook component 107 from the loop component 108 and thereby the hook component 107 is protected from being easily curled.

With the fastening system disclosed in Reference 2, however, should an engagement strength between the hook component 107 and the loop component 108 is higher than tear strength of the base sheet 105, it is likely that the hook component 107 could not be disengaged from the loop component 108 in the non-joining area 115 and, as a result, the base sheet 105 might be torn apart along the border 127 between the joining area 114 and the non-joining area 115.

SUMMARY OF THE INVENTION

It is an object of the present invention to provide a fastening system for a wearing article provided with a hook component and a loop component so improved that the hook component can be protected from being easily curled and the base sheet is protected from being torn as the hook component is disengaged from the loop component.

According to the present invention, there is provided a fastening system for a wearing article comprising: a first waist region corresponding to one of front and rear waist regions and having transversely opposed first side edge portions; a second waist region corresponding to the other of the front and rear waist regions and having transversely opposite second side edge portions; a crotch region extending between said first and second waist regions; hook carrying side edge portions provided along the transversely opposite first side edge portions and having respective hook components secured thereto; and loop carrying side edge portions provided along the transversely opposite second side edge portions and having respective loop components secured thereto which are detachably engageable with the respective hook components.

The present invention further comprises each of the hook carrying side edge portions comprising a first sheet section extending outward from each of the first side edges, a second sheet section being contiguous to an outer side edge of the first sheet section and extending toward each of the transverse side edges, a joining area extending in parallel to and spaced from the outer side edge so as to join the first sheet section to the second sheet section, and a non-joining area surrounded by the joining area, the first and second sheet sections and the outer side edge; and each of the hook components has first and second side edges extending in parallel to the outer side edge and is secured to one of the first sheet section and the second sheet section in such a manner that the first side edge lies in the joining area while the second side edge lies in the non-joining area.

According to one preferred embodiment of the invention, the first sheet section and the second sheet section are formed from a unitary sheet element and the unitary sheet element is folded back along the outer side edge to form each of the hook carrying side edge portions.

According to another preferred embodiment of the invention, at least one of the first sheet section and the second sheet section is formed in the non-joining area with at least one slit including a directional component which is parallel to the outer edge.

According to still another preferred embodiment of the invention, the hook component comprises a base sheet made of thermoplastic resin and a plurality of hook elements protruding from a top surface of the base sheet, the first and second sheet sections are formed from a nonwoven fabric containing thermoplastic resin fibers, both the base sheet and the nonwoven fabric have a tear strength being relatively low in one direction and relatively high in a direction orthogonal to the one direction, and the hook component is secured to one of the first and second sheet section in such a manner that the one direction in which the base sheet exhibits a relatively low tear strength does not coincide with the one direction in which the nonwoven fabric exhibits a relatively low tear strength.

According to further another preferred embodiment of the invention, a reinforcing sheet is secured to the base sheet.

According to the present invention, the base sheet for the hook component is secured to one of the first and second sheet sections and thereby reinforced by a nonwoven fabric constituting the first and second sheet sections. In this way, the hook component is protected from being torn apart in the course of disengaging the hook component from the loop component.

The first and second sheet sections cooperating with the outer side edge to surround the non-joining area are deformable in response to a force oriented to disengage the hook component from the loop component exerted on the outer side edge being contiguous to these first and second sheet sections so as to cover the outer side edge of the hook component and thereby to protect the hook component against being easily curled.

When the first and second sheet sections cooperating with the outer side edge to surround the non-joining area are further entrained during deformation due to the force oriented to disengage the hook component from the loop component, such force functioning to disengage the hook component from the loop component is divided into the force component oriented toward the second side edge of the hook component and the force component oriented toward the border between the non-joining area and the joining area. Consequentially, the force functioning for disengagement of the hook component is correspondingly weakened and the hook component is protected against being easily curled.

BRIEF DESCRIPTION OF THE DRAWINGS

FIG. 3 is a schematic diagram illustrating the fastening system, in which

DETAILED DESCRIPTION OF THE PREFERRED EMBODIMENTS

Figure 1:
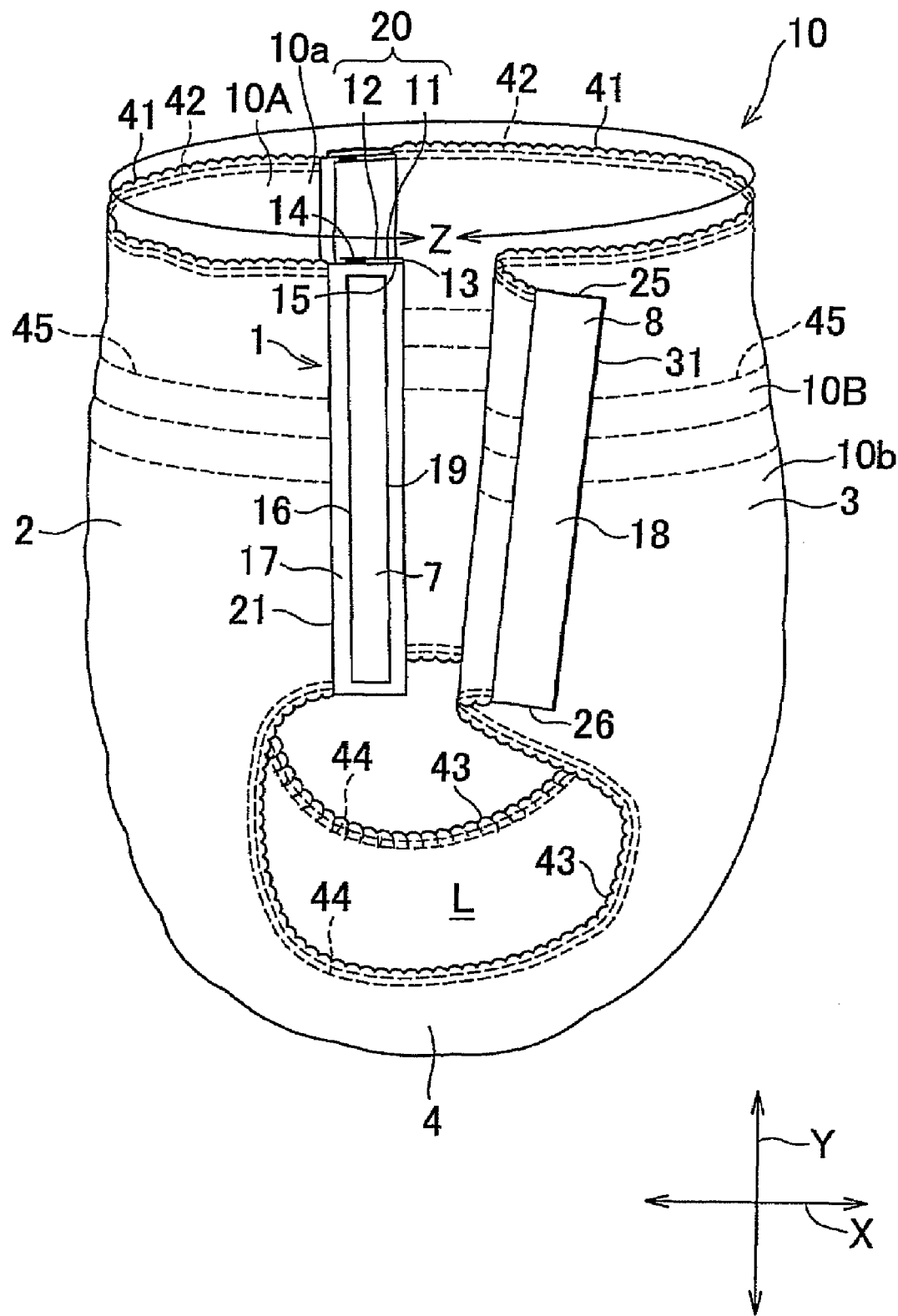
FIG. 1 is a perspective view of a diaper with its front and rear waist regions separated from each other on one side of their transversely opposite side edge portions.

Details of a fastening system 1 for the wearing article according to the present invention will be more fully understood from the description given hereunder exemplarily with respect to the case of a diaper 10 with reference to the accompanying drawings. The diaper 10 shown in FIG. 1 in a perspective view comprises a longitudinal direction Y, a transverse direction X, a waist surrounding direction Z, a liquid-permeable body side liner 10A defining a body side surface 10a, a liquid-impermeable outer sheet 10B defining a garment side surface 10b and a liquid-absorbent core (not shown) interposed the body side liner 10A and the outer sheet 10B, and further comprises a front waist region 2, a rear waist region 3 and a crotch region 4 extending between these two regions 2, 3. Waist surrounding elastic elements 42 are attached under tension along a waist hole defining edges 41 of the front and rear waist regions 2, 3 while leg surrounding elastic elements 44 are attached under tension along a pair of leg hole defining edges 43. In addition, the front and rear waist regions 2, 3 are provided with auxiliary elastic elements 45 attached under tension thereto so as to extend circumferentially and to provide a good fit of the diaper 10 to the wearer's body.

The fastening system 1 for the diaper 10 comprises hook carrying side edge portions 17 provided along the transversely opposite side edge portions 21 of the front waist region 2 to which respective hook components 7 are permanently bonded and loop carrying side edge portions 18 provided along the transversely opposite side edge portions 31 to which respective loop components 8 are permanently bonded.

As will be appreciated, both the hook component 7 and the loop component 8 constitute a so-called mechanical fastener adapted to be detachably engaged with each other. When the diaper 10 is put on the wearer's body, the loop carrying side edge portions 18 may be pressed against the associated hook carrying side edge portions 18. When the diaper 10 is taken off from the wearer's body, for example, the upper ends 25 of the loop carrying side edge portions 18 including the loop components 8 may be gripped by the wearer's fingers and then the loop components 8 may be sequentially disengaged from the hook component 7.

Each of the hook carrying side edge portions 17 is formed of a unitary sheet element 20 extending outward from the associated one of the transversely opposite side edge portions 21 of the front waist region, then folded back onto the side edge 21 along a line extending in parallel to the side edge 21 so as to define an outer side edge 13 of this hook carrying side edge portions 17 and provided with the hook component 7 so as to protrude outward with respect to the diaper wearer's body.

A section of the sheet element 20 extending from the side edge 21 of the front waist region 2 to the outer side edge 13 is referred to herein as a first sheet section 11 and the remaining section of the sheet element 20 extending from the outer side edge 13 back to the side edge 21 is referred to herein as a second sheet section 12. It should be understood that the sheet element 20 preferably comprises a fibrous nonwoven fabric containing thermoplastic resin fibers.

Figure 2:
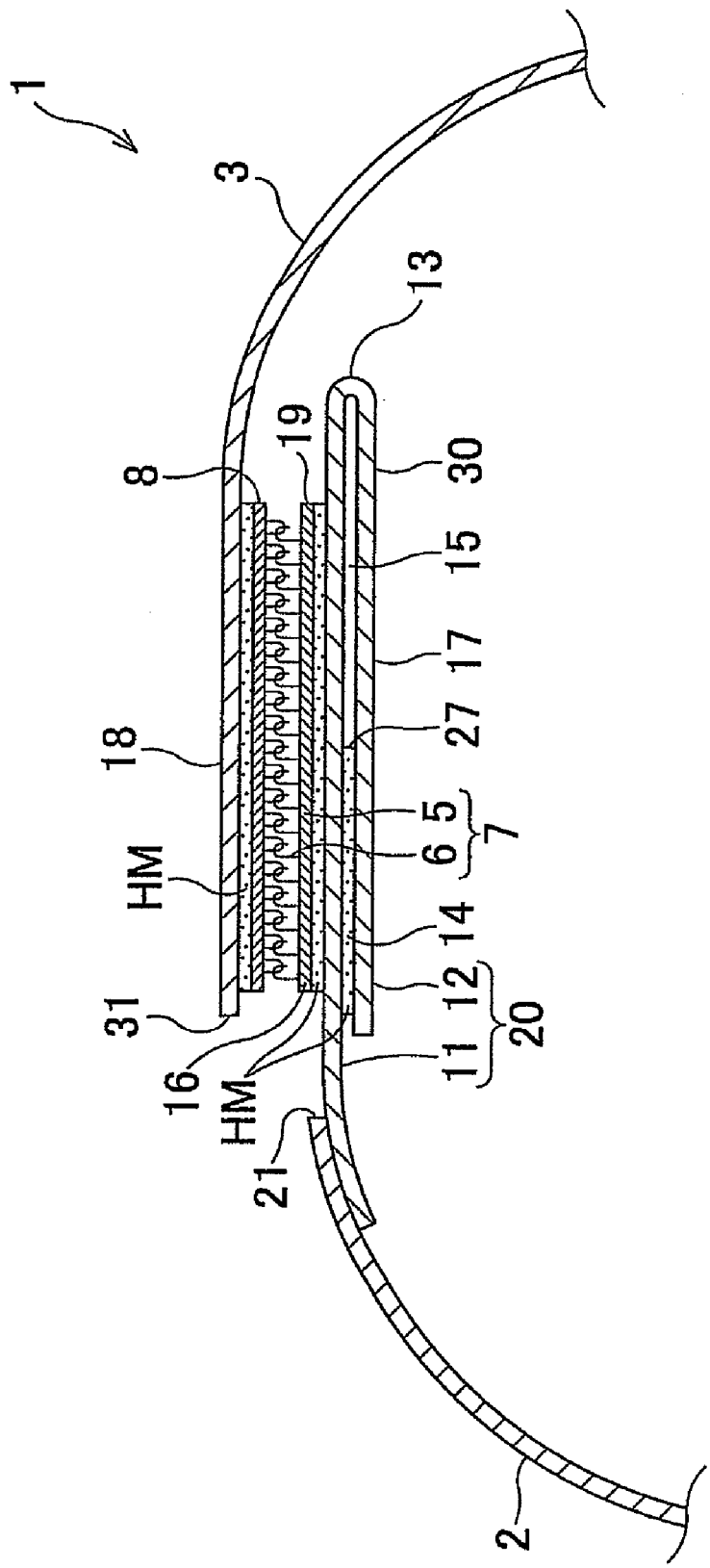
FIG. 2 is a diagram schematically illustrating an embodiment of the fastening system according to the present invention.

As schematically illustrated in FIG. 2, the first and second sheet sections 11, 12 are joined together in a joining area 14 extending in parallel to and spaced apart from the outer side edge 13 by means of hot melt adhesive HM but free from each other in a non-joining area 15 surrounded by the first and second sheet sections 11, 12 and the outer side edge 13.

The hook component 7 comprises a base sheet 5 made of thermoplastic resin and a plurality of hook elements 6 protruding from a top surface of the base sheet 5. The base sheet 5 has a first side edge 16 extending in parallel to the associated one of the transversely opposite side edge portions 21 of the front waist region and a second side edge 19 opposed to the first side edge 16. The base sheet 5 is permanently bonded to the first sheet section 11 by means of hot melt adhesive HM so that the first side edge 16 may overlie the joining area while the second side edge 19 may overlie the non-joining area 15.

With such an arrangement, hot melt adhesive HM cooperates with the nonwoven fabric constituting the first sheet section 11 to reinforce the base sheet 5 and thereby to eliminate the possibility that the hook component 7 might be torn apart when the loop component 8 is disengaged from the hook component 7. To achieve this, the nonwoven fabric preferably has a tear strength higher than a tear strength of the hook component 7. The possibility that the hook component 7 might be torn apart can be more reliably eliminated by bonding a reinforcing sheet (not shown) such as a nonwoven fabric or plastic film to the base sheet 5 prior to permanently bonding the base sheet 5 to the first sheet section 11 constituting the hook carrying side edge portion 17. Hot melt adhesive HM is preferably applied substantially over the whole area of the base sheet 5.

Generally, the base sheet 5 made of a thermoplastic resin exhibits a relatively low tear strength in the direction of extrusion for sheet forming. Specifically, if the thermoplastic resin is extruded in the direction parallel to the direction in which the side edge 21 of the waist region extend (i.e., the direction in which the loop carrying side edge portion extends from its upper end 25 to its lower end 26), the base sheet 5 would be disadvantageously apt to be torn apart when the loop component 8 is disengaged from the hook component 7.

The sheet element 20 made of a nonwoven fabric also may exhibits a relatively low tear strength in the direction of extrusion for sheet forming. In such case, it is essential to avoid such a relationship that the direction in which the base sheet 5 exhibits the lower tear strength coincides with the direction in which the sheet element 20 exhibits the lower tear strength in order to enhance a desired reinforcing effect of the sheet element 20 for the base sheet 5 and thereby to protect the base sheet 5 further reliably from being easily torn apart.

The hook component 7 has a tear strength preferably in a range of 0.3 to 3.0 N, more preferably in a range of 0.5 to 1.2 N. If the tear strength of the hook component 7 is less than 0.3 N, it will be impossible to assure a level of the tear strength required for the hook component 7 to be manufactured and practically used without any anxiety. If the tear strength of the hook member 7 exceeds 3.0 N, the base sheet 5 of the hook component 7 will become undesirably stiff and increase a feeling of discomfort during use of the diaper. The nonwoven fabric constituting the sheet member 20 has a tear strength preferably in a range of 3.5 to 25 N, more preferably in a range of 5.0 to 17 N. If the tear strength is less than 3.5 N, it will be impossible to assure a level of the tear strength required for the sheet element 20 to serve as the reinforcing material. If the tear strength exceeds 25 N, the nonwoven fabric constituting the sheet element 20 will become undesirably stiff and increase a feeling of discomfort during use of the diaper.

The tear strength is measured in a manner as follows: Assuming that the direction in which the base sheet 5 or the nonwoven fabric of the hook carrying side edge portion 7 to be tested was sheet-formed corresponds to its longitudinal direction and the direction orthogonal to this corresponds to its transverse direction, a sample of the hook carrying side edge portion 17 having a length of 50 mm and a width of 30 mm is prepared. Then a cutter is used to form the sample with a slit having a length of 20 mm long in the longitudinal direction from a point on one end of the sample bisecting the width of this sample. Along the slit, the sample is bifurcated and respective finger-grip margins of approximately 15 mm are attached to a tensile tester with an inter-chuck distance of 10 mm. Then the respective finger-grip margins are pulled in opposite directions at a pulling rate of 300 mm/min and a value of the maximum load measured until the sample is broken is determined as the tear strength of this sample.

Referring to FIG. 2, the arrangement in which hook elements of the hook components 7 of the hook carrying side edge portion 17 protrude outward with respect to the wearer may cause a problem since the outer side edge 13 of the hook carrying side edge portion 17 is present inside the diaper 10 and apt to come in contact with the wearer's skin. Consequentially, if the wearer twists his or her body or inserts his or her fingers between the diaper 10 and his or her body and slidably moves these fingers circumferentially along his or her waistline, a force oriented to disengage the hook component 7 from the loop component 8 may be exerted on the outer side edge 13.

Figure 3A:
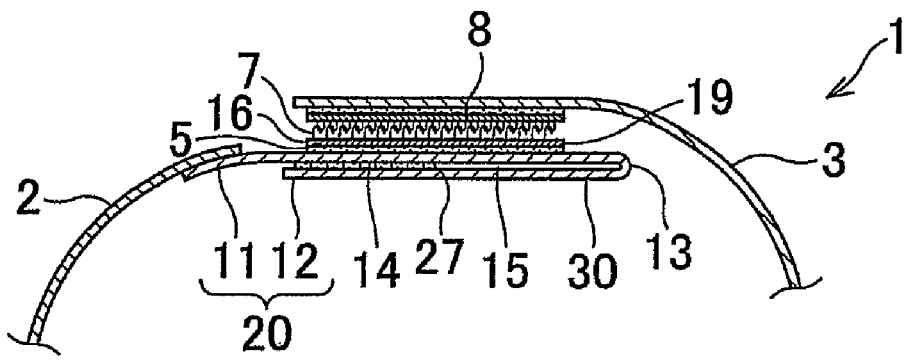
FIG. 3A illustrates a state of the fastening system before a force is exerted on an outer end, and FIG. 3B as well as FIG. 3C illustrates a state of the fastening system when a force is exerted on the outer end.
Figure 3B:
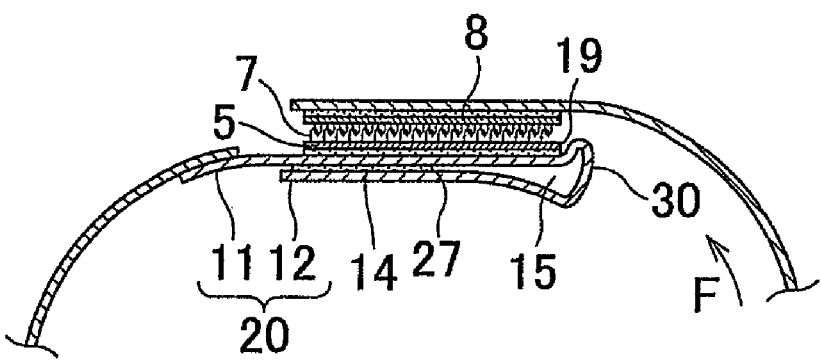

With the fastening system 1 according to the present invention, even if a force oriented to disengage the hook component 7 from the loop component 8 is exerted on the outer side edge 13, a possibility that the hook component 7 might be partially or wholly disengaged from the loop component 8 can be effectively avoided as will be described hereinafter with reference to FIG. 3A through FIG. 3C. FIG. 3A is a schematic diagram illustrating a state before the force F oriented to disengage the hook component 7 from the loop component 8 is exerted on the outer side edge 13 while FIG. 3B and FIG. 3C are schematic diagrams illustrating states under such force F exerted on the outer side edge 13.

As illustrated in FIG. 3A, a portion of the sheet element 20 extending from the outer side edge 13 to the second side edge 19 of the base sheet 5 as well as a portion of the sheet element 20 extending from the outer side edge 13 to a border 27 between the non-joining area 15 and the joining area 14 is not joined to the other elements, i.e., free. Consequentially, these portions are deformable under an external force. These deformable portions will be collectively referred to hereinafter as a deformable area 30.

When the wearer's movement causes the force F oriented to disengage the hook component 7 from the loop component 8 is exerted on the outer side edge 13, the latter is pushed by the force F and the deformable area 30 begins to be deformed since the outer side edge 13 extends outward beyond the second side edge 19 of the base sheet 5 constituting the hook component 7 as illustrated by FIG. 3A. Thus, the deformable area 30 is deformed so as to cover the second side edge 19 of the base sheet 5 constituting the hook component 7 as illustrated in FIG. 3B. If the force F continues to be exerted on the outer side edge 13, the deformable area 30 of the sheet element 20 will be displaced but remain to cover the second side edge 19 and thereby prevent the hook component 7 from being easily curled or disengaged from the loop component 8. At this time point, the force F is oriented also to press the hook component 7 against the loop component 8.

Figure 3C:
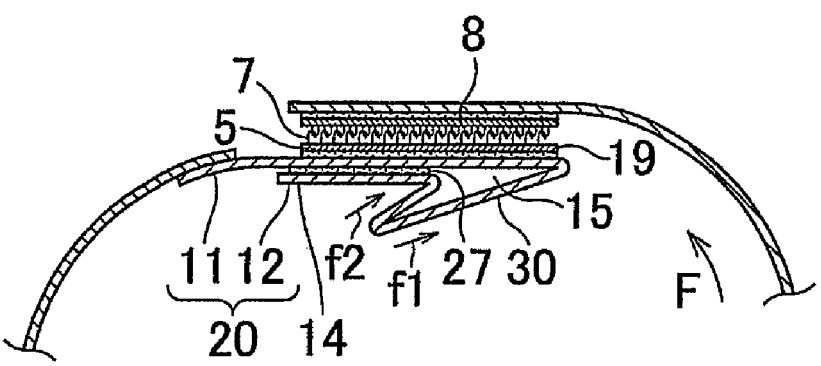

The deformable area 30 is deformed under an entraining effect of the force F oriented to disengage the hook component 7 from the loop component 8 until the deformable area 30 takes a position as illustrated in FIG. 3C. Thereupon, the force F is divided into a component f1 oriented toward the second side edge 19 of the hook component 7 and a component f2 oriented toward the border 27 between the non-joining area 15 and the joining area 14. This means that the force exerted on the outer side edge 13 is reduced and the possibility of curling as well as disengagement of the hook component 7 can be alleviated.

Figure 4:
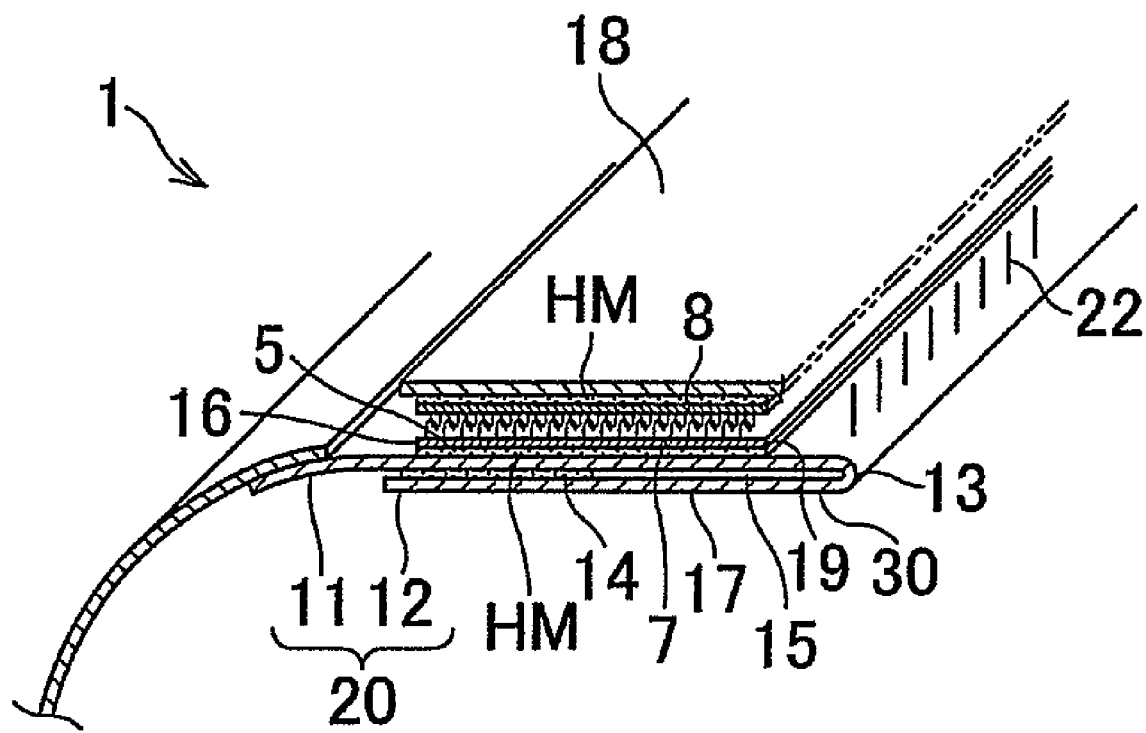
FIG. 4 is a schematic diagram illustrating another embodiment of the fastening system according to the present invention.
Figure 5A:
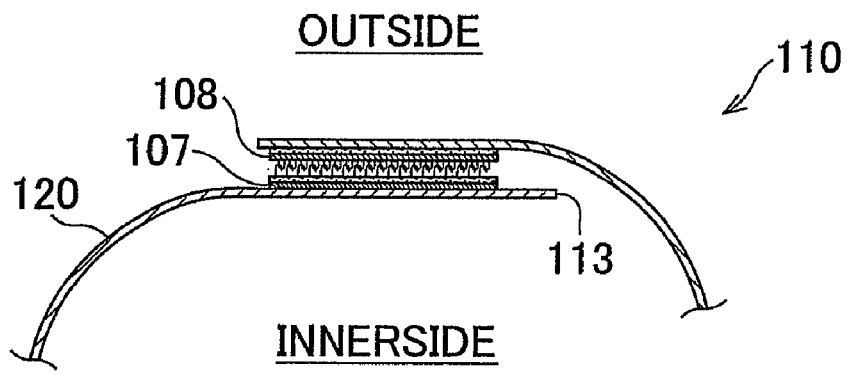
FIG. 5 is a schematic diagram illustrating the fastening system of prior art, in which FIG. 5A as well as FIG. 5B illustrates the fastening system disclosed in Reference 1
FIG. 5C illustrates the fastening system disclosed in Reference 2.
Figure 5B:
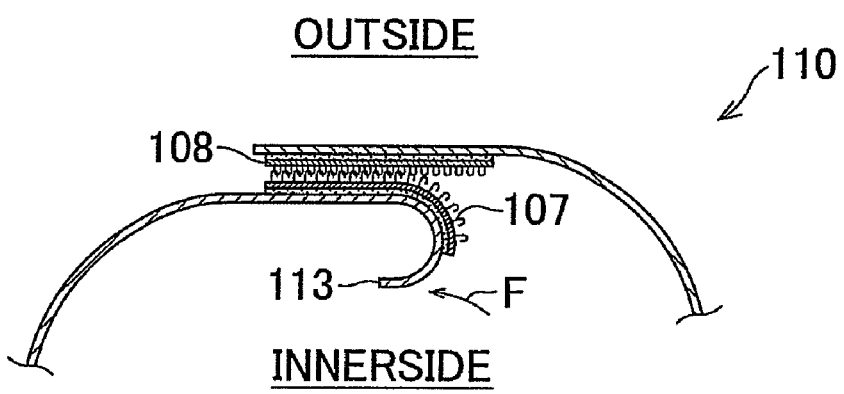
Figure 5C:
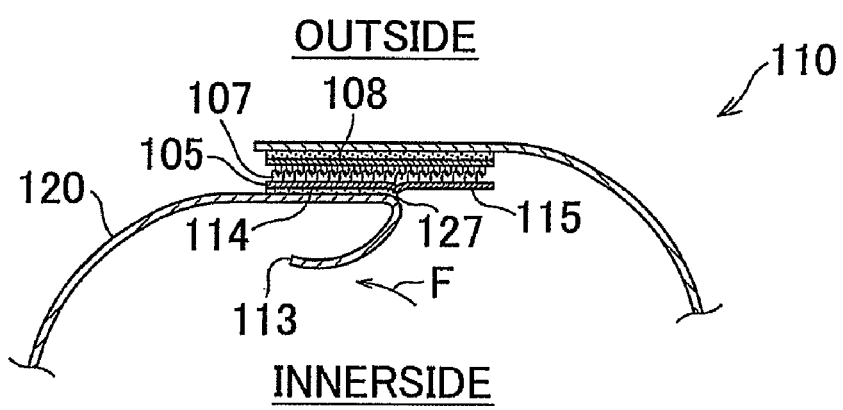

FIG. 4 is a schematic diagram illustrating an alternative embodiment of the fastening system 1. According to this alternative embodiment, the first sheet section 11 of the sheet element 20 on which the hook components 7 are permanently planted is formed with a plurality of slits 22 each extending obliquely with respect to the outer side edge 13.

According to this embodiment, the area of the first sheet section 11 in which the slits 22 are formed is stretched as the deformable area 30 is entrained and deformed under the force F oriented to disengage the hook component 7 from the loop component 8. As a result, the component of the force oriented toward the second side edge 19 of the hook component 7 is sufficiently reduced to protect the hook component 7 against being easily curled or disengaged from the loop component 8. The elastic components such as the waist-surrounding elastic elements 42 and the auxiliary elastic elements 45 are processed preferably in such a manner that no elasticity should be expressed by these elastic elements immediately under the loop component 8. This can be achieved by cutting, coating with a hot melt adhesive or chemical treatment of these elastic elements such as the auxiliary elastic elements 45 lying immediately under the loop component 8. In this way, the anxiety that the loop component 8 might get wrinkles and a bond strength between the loop component 8 and the hook component 7 might be deteriorated can be reliably eliminated.

While the fastening system according to the present invention has been described above on the basis of the preferred embodiments thereof, the present invention is not limited to such embodiments but may be exploited in the other various manners. For example, it is possible without departing from the spirit and the scope of the invention to arrange hook elements of the hook component 7 so as to protrude not outward but inward. With this arrangement, it is unlikely that the hook component 7, if curled, might damage the wearer's garment or bedclothes.

It is also possible without departing from the spirit and the scope of the invention to form the hook carrying side edge portion 17 from a pair of sheets instead of the unitary sheet element. In this case, these two sheets may be bonded to each other along edges thereof destined to define the outer side edge 13. However, it will be appreciated that the illustrated embodiment having the hook carrying side edge portion 17 formed of the unitary sheet element is preferred to the alternative embodiment as has been described just above since the deformable area 30 including none of joined portions is smoothly deformable. In addition, bonding of the first and second sheet sections 11, 12 as well as permanent bonding or planting of the hook component 7 may be carried out not only by means of hot melt adhesive HM but also by means of the other well known technique such as heat sealing or ultrasonic sealing. Furthermore, the loop component 8 comprising the loop elements of the mechanical fastener may be replaced by a nonwoven fabric adapted to be engaged with the hook component.

The entire discloses of Japanese Patent application No. 2006-187146 filed on Jul. 6, 2006 including specification, drawings and abstract are herein incorporated by reference in its entirety.

What is claimed is:

1. A fastening system for a wearing article comprising:
   a first waist region corresponding to one of front and rear waist regions and having transversely opposed first side edge portions;
   a second waist region corresponding to the other of said front and rear waist regions and having transversely opposite second side edge portions;
   a crotch region extending between said first and second waist regions;
   hook carrying side edge portions provided along said transversely opposite first side edge portions and having respective hook components secured thereto;
   loop carrying side edge portions provided along said transversely opposite second side edge portions and having respective loop components secured thereto which are detachably engageable with said respective hook components;
   each of said hook carrying side edge portions comprising a first sheet section extending outward from each of said first side edges, a second sheet section being contiguous to an outer side edge of said first sheet section and extending toward each of said transverse side edges, a joining area extending in parallel to and spaced from said outer side edge so as to join said first sheet section to said second sheet section, and a non-joining area surrounded by said joining area, said first and second sheet sections and said outer side edge; and
   each of said hook components has first and second side edges extending in parallel to said outer side edge and is secured to one of said first sheet section and said second sheet section in such a manner that said first side edge lies in said joining area while said second side edge lies in said non-joining area.

2. The fastening system for the wearing article defined by claim 1 wherein said first sheet section and said second sheet section are formed of a unitary sheet element and said unitary sheet element is folded back along said outer side edge to form each of said hook carrying side edge portions.

3. The fastening system for the wearing article defined by claim 1 wherein at least one of said first sheet section and said second sheet section is formed in said non-joining area with at least one slit including a directional component which is parallel to said outer side edge.

4. The fastening system for the wearing article defined by claim 1 wherein said hook component comprises a base sheet made of thermoplastic resin and a plurality of hook elements protruding from a top surface of said base sheet; said first and second sheet sections are formed of a nonwoven fabric containing thermoplastic resin fibers; both said base sheet and said nonwoven fabric have a tear strength being relatively low in one direction and relatively high in a direction orthogonal to said one direction; and said hook component is secured to one of said first and second sheet section in such a manner that said one direction in which said base sheet exhibits a relatively low tear strength does not coincide with said one direction in which said nonwoven fabric exhibits a relatively low tear strength.

5. The fastening system for the wearing article defined by claim 4 wherein a reinforcing sheet is secured to said base sheet.

\* \* \* \* \*